United States Patent [19]

Spellicy

[11] 4,412,445
[45] Nov. 1, 1983

[54] RESONANT SPECTROPHONE SYSTEM NOISE ELIMINATION

[75] Inventor: Robert L. Spellicy, Las Cruces, N. Mex.

[73] Assignee: OptiMetrics, Inc., Ann Arbor, Mich.

[21] Appl. No.: 296,774

[22] Filed: Aug. 27, 1981

[51] Int. Cl.³ .......................................... G01N 29/02
[52] U.S. Cl. .......................................... 73/24; 73/579
[58] Field of Search .................................. 73/24, 579

[56] References Cited

U.S. PATENT DOCUMENTS 4,163,382  8/1979  Amer .................................... 73/24
4,280,823  7/1981  Sozonntagh ........................... 73/24

*Primary Examiner*—Anthony V. Ciarlante
*Attorney, Agent, or Firm*—Stephenson & Boller

[57] ABSTRACT

A resonant spectrophone system has a laser arranged to direct a laser beam into a chamber containing gas to be analyzed wherein absorption data relative to the gas constituents is obtained by detecting pressure variations within the chamber. The laser is operated such that the laser beam passing through the chamber generates a resonant wave therein. Pressure variations within the chamber are monitored at locations corresponding to nodal and/or peak points of the resonant wave. The nodal point signals represent background noise and are subtracted from the peak point signals to remove noise components from the peak point signals or out-of-phase nodal signals are subtracted to perform this function and thereby yield signals which more accurately represent the absorption data relative to the gas constituents.

8 Claims, 7 Drawing Figures

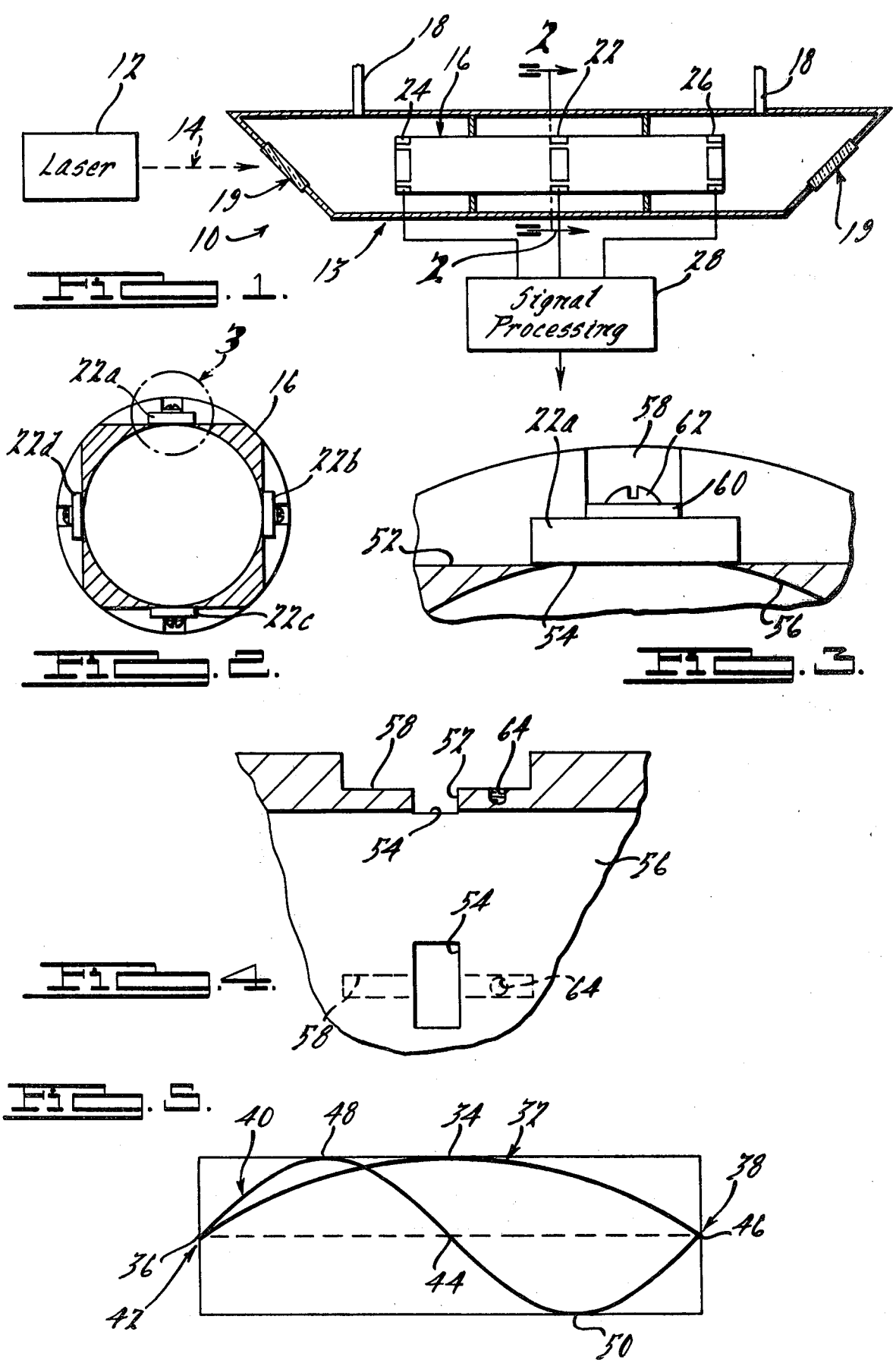

RESONANT SPECTROPHONE SYSTEM NOISE ELIMINATION

BACKGROUND AND SUMMARY OF THE INVENTION

The present invention relates to spectrophone or photo-acoustic systems and is more specifically concerned with a new and improved arrangement for eliminating noise from the spectrophonic measurement of gas absorption data.

Laser absorption spectrometers measure gas samples for the purpose of determining the absorption characteristics of the gas constituents. Measured absorption characteristics can be used to identify the presence of specific constituents in the gas. Laser absorption spectrometers can also be used to investigate the attenuation which is caused by certain gas constituents on radiation transmission through the gas.

One type of laser absorption spectrometer heretofore known comprises a sample chamber containing the gas to be analyzed. A laser beam is directed into the chamber through an appropriate window. Constituents of the gas will absorb energy of the laser beam in certain characteristic fashions, and subsequently deactivate giving rise to corresponding pressure changes within the chamber. These pressure changes can be detected to provide an indication of the absorption characteristics. The absorption characteristics in turn can be used to identify constituents in the sample and/or to ascertain the effect of the gases on the transmission of laser beam energy through the gas. In prior types of laser absorption spectrometers, pressure responsive sensors, or transducers, are positioned in the chamber to sense the pressure variations and to provide corresponding electrical signals indicative of these pressure variations.

In connection with the usage of such prior devices, the problem of background noise has been observed. It has been found that actual commercial laser absorption spectrometers have heretofore not possessed the required sensitivity for making certain types of measurements. Particularly in the field of measuring low absorption coefficients, background noise becomes a limiting factor especially at low total pressures.

The most sensitive photo-acoustic systems currently in use employ resonant chambers, or cavities, containing dynamic, or electret, microphones placed in such a way as to detect maximum pressure variations in the cavities. Since the detection limits of these systems are primarily a function of background noise level, differential type systems have heretofore been used in attempts to cancel the effect of background noise from the measured signal. These differential systems have typically consisted of two cavities in series, isolated from each other by an optical window. One of the cavities is filled with a non-absorbing, or reference, gas while the other is filled with the gas to be studied. Signals from the reference gas are taken as the background, or reference, signal and are subtracted from the signal obtained from the other chamber. A disadvantage of this arrangement is that it requires the use of two separate chambers (or sub-chambers) and in addition requires matching the response characteristics of the two chambers if proper background noise cancellation is to be realized. In addition, the background noise frequently limiting the detectivity of photo-acoustic systems is that arising from absorption of radiation in the optical windows of the system. Consequently, differential systems requiring a window between the two separate chambers (or sub-chambers) must completely cancel these relatively large window signals if they are to achieve their ultimate detection limit. An example of a differential system of this type is disclosed in U.S. Pat. No. 4,058,725, dated Nov. 15, 1977.

Other types of laser absorption spectrometers are disclosed in U.S. Pat. No. 3,793,525, dated Feb. 19, 1974; U.S. Pat. No. 3,727,050, dated Apr. 10, 1973; and U.S. Pat. No. 3,659,452, dated May 2, 1972.

The present invention is directed to a new and improved spectrophone containing an improved arrangement for elimination of background noise. One advantage of the invention is that only a single chamber is required thereby eliminating the complexity of having matched dual chambers of the differential type system described above.

A further advantage of the invention is that is does not require optical windows in the system for proper operation.

Briefly, pursuant to principles of the present invention, gas within a test chamber is subjected to an impingent laser beam from a laser which is operated in a manner as to impart a frequency to the chamber substantially at a resonant frequency of the chamber. This mode of operation sets up a resonant standing wave within the chamber possessing peak and nodal points. Sensors are located at the nodal and/or peak points, and signals from the sensors are utilized to develop the absorption signal; specifically, nodal point signals or peak signals 180 degrees out of phase are subtracted from one another. In the case of nodal point subtraction, the nodal point signals are predominantly the result of background acoustical noise and when substracted from the peak point signals serve to eliminate background noise from the peak point signals. In the case of subtraction of peak signals 180° out of phase, the subtraction enhances the resonant component while canceling signals not possessing this specific phase relationship. In either case the result is a single chamber photo-acoustic detector with substantially improved noise rejection characteristics and a lowered detection threshold.

In the specific example of the invention disclosed herein, the resonant chamber, or cavity, is of an elongated cylindrical shape and the gas is excited at a longitudinal resonant frequency of the chamber. A set of microphones is located at the longitudinal midpoint of the chamber, and additional sets of microphones are located at or near the longitudinal ends of the chamber. When the gas is excited at the fundamental longitudinal mode frequency of the chamber, the center set of microphones measure the peak pressure variation while the sets of microphones at or near the ends of the chamber measure the pressure nodes. The measurements at the pressure nodes theoretically should be zero, and hence, any signal obtained other than zero is considered indicative of background noise. By averaging the signals from the end sets of microphones and subtracting the result from the average obtained at the center set of microphones, the background noise component is eliminated from the peak pressure measurement. The invention yields a substantial improvement in the signal-to-noise ratio of the system with attendant lower detection threshold capability which is particularly useful, as explained above, for measuring low absorption coefficients.

The invention also does not appreciatively impair the Q of the system and it avoids the adverse effect of the 1/f fall-off of the pressure signal characterizing other types of systems.

The foregoing features, advantages, and benefits of the present invention, along with additional ones, will be seen in the ensuing description and claims which should be considered in conjunction with the accompanying drawings. The drawings disclose a preferred embodiment of the invention according to the best mode contemplated at the present time for carrying out the invention.

BRIEF DESCRIPTION OF THE DRAWINGS

FIG. 1 is a diagrammatic view of an open ended resonant spectrophone system embodying principles of the present invention.

FIG. 2 is a transverse cross-sectional view slightly enlarged, of the sub-chamber portion of the system taken in the direction of line 2—2 in FIG. 1.

FIG. 3 is an enlarged fragmentary view taken in circle 3 of FIG. 2 to illustrate still further detail.

FIG. 4 is a fragmentary longitudinal view of a portion of the sub-chamber illustrating additional detail.

FIG. 5 is a graph plot useful in illustrating principles of the invention.

DESCRIPTION OF THE PREFERRED EMBODIMENT

Figure 6:
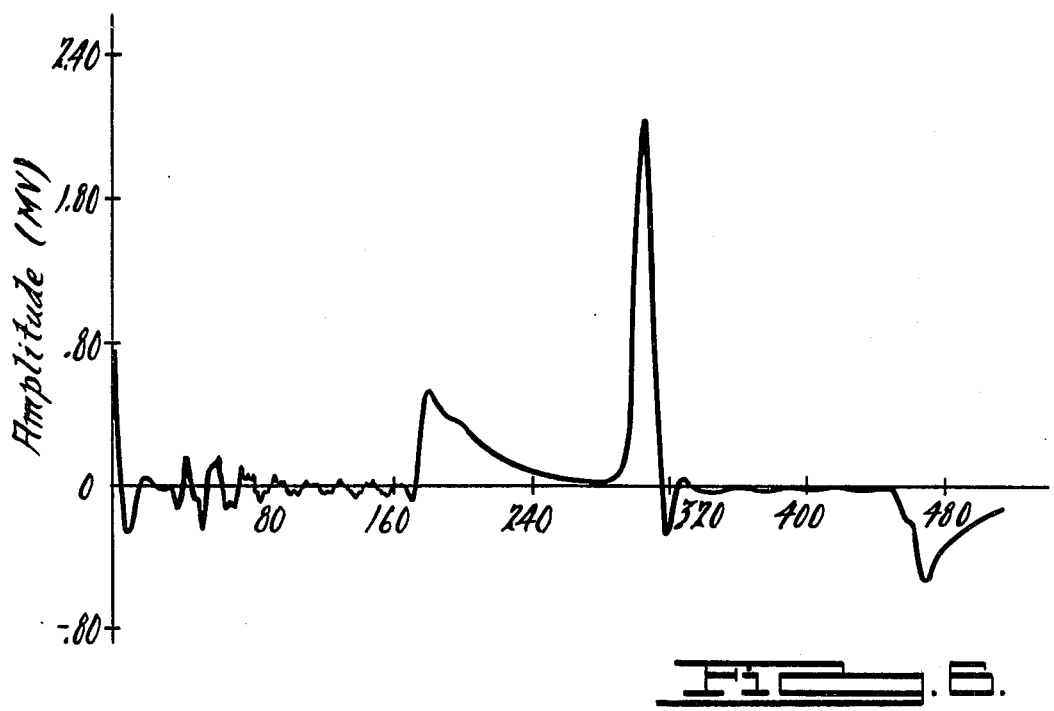
FIGS. 6 and 7 are comparative graph plots useful in illustrating the improved performance which results from the present invention.

FIG. 1 illustrates an example of a spectrophone system 10 embodying principles of the present invention. The system includes a conventional laser source 12 which supplies a laser beam 14 directed longitudinally into the interior of a walled cylindrical sub-chamber 16 containing a gas sample. Appropriate piping 18 is utilized to convey the gas sample to and from the outer-chamber 13 and appropriate windows 19 are arranged at the ends of chamber 13 to provide for transmission of laser beam 14 through chamber 16.

Pursuant to the invention, microphones are associated with sub-chamber 16 and in the example of the disclosed embodiment, three sets of microphones 22, 24 and 26 are employed. Each set of microphones comprises four individual microphones which are uniformly arranged at 90° circumferential intervals with respect to the cylinder (FIG. 2). The microphone set 22 is positioned at the longitudinal midpoint while the microphone sets 24 and 26 are positioned at or near the longitudinal ends. The signals from the respective microphone sets are supplied via electrical conductors to electrical circuitry and equipment 28 which process the signals in a suitable manner in order to develop the desired data relating to the absorption characteristics of the gas in the chamber.

In operation of the system, gas whose absorption characteristics are to be studied is introduced into chamber 13. In the example of the disclosed embodiment, the resonant subchamber is an elongated cylinder and the laser beam is directed longitudinally through the chamber. By operating the laser such that the gas is excited at a frequency corresponding substantially to the longitudinal resonant frequency of the sub-chamber, a longitudinal resonant wave is established within the sub-chamber. The resonant excitation may be created by either of the well-known techniques of pulsing the laser or by chopping a CW laser beam. By utilizing the fundamental longitudinal resonant frequency, the peak of the resonant wave will occur at the londitudinal midpoint of the chamber. Hence, the microphone set 22 will detect this peak signal. However, it will be recognized that in actuality the gas signal output from the microphone set 22 will contain both true absorption signal data at well as noise.

The microphone sets 24 and 26 at or near the longitudinal ends of the chamber are provided to monitor noise alone. Theoretically in the absence of noise, the resonant wave will have nodal points at or near the open ends of the subchamber 16 at which zero amplitude signal measurements should be obtained. However, the reality of noise will cause non-zero signals to be detected by the microphone sets 24 and 26. If these signals are averaged a noise measurement is obtained. The noise may be due to any of a number of possible sources. If the noise signal derived from the microphone sets 24 and 26 is subtracted from the signal derived from the microphone set 22, then the resultant signal will closely approximate the true absorption signal data because a substantial amount of noise has been removed. In this way, the detection threshold and signal-to-noise ratio for the system are improved. This is very important when gases of low absorption are being analyzed; it is also important where the laser is being pulsed since pulsing may generate electrical noise detected by the microphones. Hence, the present invention achieves a significant improvement in the performance of photoacoustic detectors.

FIG. 5 is a graph plot illustrating the relationship between the resonant wave developed in the chamber and the location of the microphone sets. The graph plot identified by the reference numeral 32 constitutes an idealized longitudinal resonant wave generated within the chamber at the fundamental chamber longitudinal frequency. As can be seen, the maximum amplitude 34 occurs at the longitudinal midpoint of the chamber and this is where the microphone set 22 is positioned. The wave 32 has nodal points, 36 and 38 respectively, at or near the longitudinal ends of the chamber and this is where the microphone sets 24 and 26 are respectively positioned.

The invention recognizes that any noise which is present will be substantially equal at the respective microphone sets. Theoretically in an idealized system there would be no signal at the nodal points 36 and 38 and hence the signal at the peak point 34 would alone represent the true absorption signal data. However, the noise which is superimposed on the peak point signal will be essentially that which appears at the nodal points. Hence, by subtracting the noise signals obtained at the nodal points 36 and 38 from the signal obtained at peak point 34, the noise which is present in the peak signal is eliminated so as to yield a signal which has an improved signal-to-noise ratio over prior types of systems. Also the detectivity threshold is lower.

An advantage of using a plurality of microphones at each longitudinal location is to compensate for azimuthal variations in the pressure signal which can arise for example from corresponding variations in the laser beam profile.

In the disclosed system for developing the true absorption signal, the four individual microphone signals from each end set of microphones 24 and 26 are averaged. The two average end signals are further averaged to yield an average noise signal. The average of the four microphone signals at the center set of microphone, 22 is taken, and from this is subtracted the average noise signal to thereby yield the true absorption signal. It will be understood that the details of the actual signal processing technique are not critical to the practice of the invention. Hence, the relatively uncomplicated technique of simply averaging and subtracting has been disclosed. Other more sophisticated processing techniques can be used if desired.

While the foregoing describes one particular example it is contemplated that principles of the invention may be applied to other examples. The graph plot 40 in FIG. 5 is shown to represent the first overtone of the fundamental longitudinal resonant frequency of the chamber 16. This first overtone has three nodal points 42, 44, 46 and two peak points 48 and 50 180° out of phase with one another. The nodal points 42 and 46 are coincident with the nodal points 36 and 38 of the fundamental resonant wave; however, the remaining nodal point 44 is at the midpoint of the chamber while the peaks 48, 50 are approximately at the one-quarter and three-quarter length locations. Absorption data measurement for this mode may be obtained by locating microphones at both peak points 48 and 50. The peak point signals may be individually averaged and subtracted from one another to effectively double the signal arising from this resonant mode while canceling or partially canceling signals not possessing this specific phase relationship.

Figure 7:
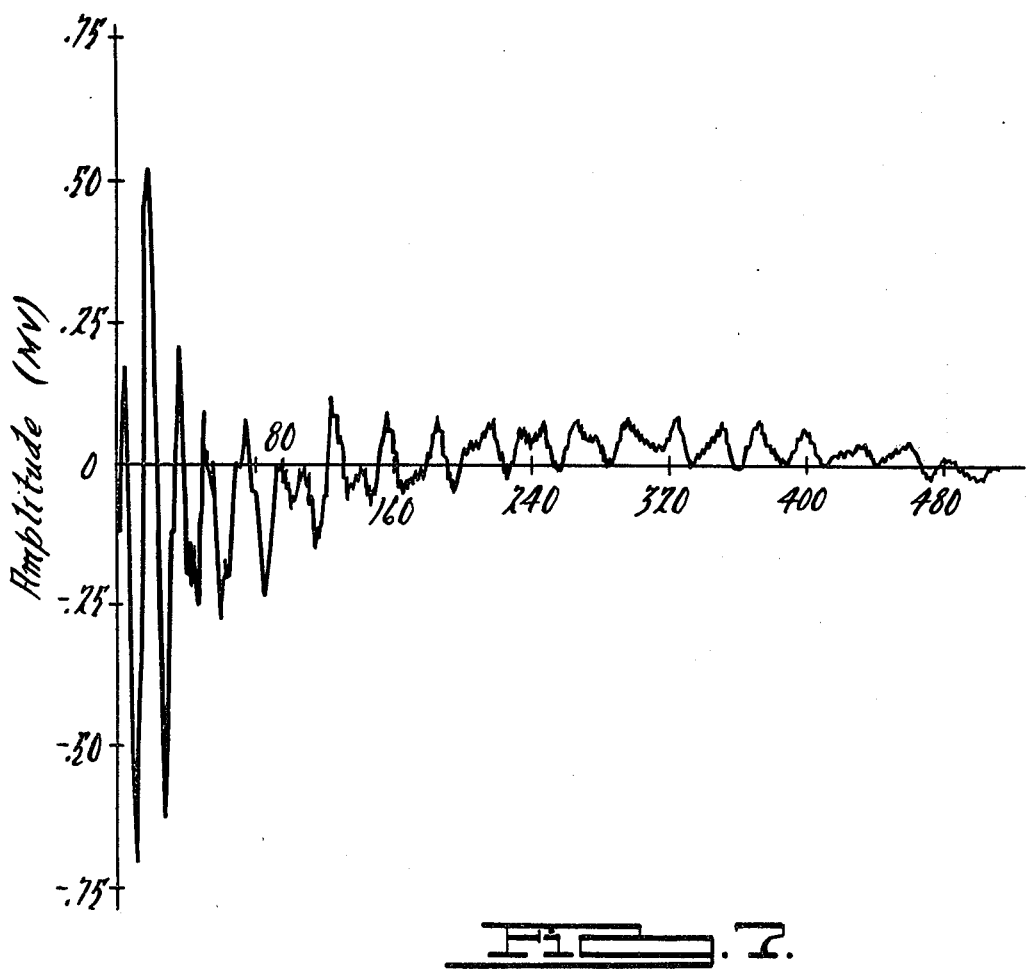

The graph plots shown in FIGS. 6 and 7 illustrate the type of improvement which can be obtained with the present invention. FIG. 6 illustrates an output wave form observed at the longitudinal midpoint of the chamber arising from a pulsed laser input without the signals from the end microphones being subtracted. The condition was obtained while the spectrophone circulating pump was being run to deliberately introduce high amplitude noise. The fill conditions were 0.434 torr $CO_2$, 75 torr total ($N_2/O_2$ buffer) with an absorption coefficient of 2.63 $km^{-1}$. When the signal of FIG. 6 is corrected by subtracting from it the noise signals from the end sets of microphones, the waveform shown in FIG. 7 is obtained. As can be seen, a very significant improvement has resulted.

FIGS. 2, 3 and 4 illustrate in greater detail the arrangement for mounting the individual microphones on the cylindrical chamber 16. FIG. 2 illustrates the four microphones 22a, 22b, 22c, 22d of the center microphone set 22. The microphones are arranged at 90° circumferential intervals. The end microphone sets 24, 26 contain similarly arranged individual microphones with the corresponding microphones in each of the three microphone sets 22, 24, 26 being longitudinally aligned.

In order to optimize the performance of a photoacoustic system embodying principles of the invention it has been found desirable to minimize the intrusion of the microphones into the circular cylindrical shaped cavity. One way of minimizing the intrusion is to utilize relatively small microphones which are of a generally rectangular configuration. At each location where an individual microphone is to be mounted, a transverse slot 52 is made which passes through the wall of the cylinder so as to create a rectangular opening 54 at the inner wall surface 56 of the cylinder. The individual microphone unit is then placed to have the active area of the microphone at the opening 54. In this way the active area of the microphone is disposed in transverse cross section essentially along a very small chord of the circular inner wall surface 56, and is hence substantially flush-mounted. As can be seen in FIG. 3, the positioning of the microphone unit in this manner creates a minimal impairment of the circular cross sectional shape of the inner wall surface 56 and avoids any substantial degradation of the Q of the cavity.

The microphone unit may be retained in position by a suitable means. For example a longitudinal slot 58 of shallower depth may be made at right angles to each slot 52. A retaining clip 60 is positioned in slot 58 to overlie the microphone unit with the retaining element 60 being held in place by a screw 62 passed through a suitable aperture in clip 60 into a tapped hole 64 in the chamber wall. The specific retention arrangement is merely exemplary and it will be appreciated that other arrangements may be employed within the overall scope of the present invention.

A preferred microphone is an electret type, for example a Knowles Model BT-1834. This particular model uses an FET pre-amp which allows for matching the individual microphones in each set.

Principles of the invention may be applied to different types of spectrophone systems. For example, the invention may be practiced in the context of an evacuated chamber into which a gas sample to be analyzed is introduced or it may be an open chamber type wherein ambient air is drawn through the chamber and its content is measured. It is also contemplated that the invention may be practiced with different specific shapes of resonant chambers so long as the radiation is introduced in such a manner as to excite the chamber resonance with the microphones placed at appropriate node and/or peak locations in order to detect the resonance.

Principles of the invention can also be applied to other types of chambers. For example, consider a cylindrical chamber having both axial ends closed. The excitation in this case is such that a resonant half wave may be established within the chamber with the longitudinal midpoint of the chamber being the node, one end of the chamber being a positive maximum and the opposite end being a negative maximum. If a set of microphones is placed at one end of the chamber and another set of microphones at the opposite end, then signals representative of the positive maximum and the negative maximum may be respectively generated. These two signals may be processed to provide a true absorption signal in the same manner as discussed above for the first overtone in the open sub-chamber at FIG. 5.

The invention may be utilized for all types of fluent samples. For example, fluid substances such as gases may be studied, liquid dispersions, such as aerosols, may be studied, and solid particulate suspensions in fluid media may also be studied.

From the foregoing, it can be seen that a new and improved spectrophone system has been disclosed possessing significant advantages over other spectrophone systems. While a preferred embodiment has been disclosed, it will be appreciated that other embodiments may be indulged in within the scope of the invention as set forth in the following claims.

What is claimed is:

1. In a spectrophone system wherein radiant energy from a radiant energy source is directed into a chamber containing a fluent sample with respect to which certain absorption data is to be obtained in the presence of background noise by detecting pressure variations within the chamber and generating a signal containing both absorption data and noise components, the radiant energy having a component corresponding to an absorption characteristic of the fluent sample which is being investigated and said chamber having a geometry allowing a resonant wave to be established in the chamber, the improvement for significantly attenuating the noise component relative to the absorption data component which comprises means of creating a resonant wave in the chamber by excitation from the radiant energy source, means for monitoring pressure variations at a location within the chamber corresponding to a peak of the resonant wave to develop a corresponding peak signal containing both true absorption data and noise components, means for monitoring pressure variations at a location within the chamber corresponding to a nodal point of the resonant wave and generating a corresponding nodal signal representing background noise, and means for modifying the peak signal by the nodal signal to remove the noise component from the peak signal and yield a true absorption data signal.

2. The improvement set forth in claim 1 wherein said chamber is cylindrical in shape, the radiant energy is directed longitudinally through the cylindrical chamber, said means for monitoring pressure variations at a location within the chamber corresponding to a peak of the resonant wave created therein comprises microphonic means disposed at a location spaced from the longitudinal ends of the chamber, and said means for monitoring pressure variations at a location within the chamber corresponding to a nodal point of the resonant wave comprises microphonic means disposed at or near at least one of the longitudinal ends of the chamber.

3. The improvement set forth in claim 2 wherein said means for creating a resonant wave in the chamber comprises means for operating a laser source so as to generate a resonant wave at the fundamental resonant frequency of the chamber in the longitudinal direction and wherein said first-mentioned microphonic means is disposed at the longitudinal midpoint of the chamber.

4. The improvement set forth in claim 2 wherein each microphonic means comprises a plurality of individual microphones which are circumferentially arranged about the circumference of the chamber.

5. The improvement set forth in claim 4 wherein the active areas of the individual microphones are substantially flush with the inner wall surface of the chamber so as not to intrude significantly into the otherwise cylindrical interior of the chamber.

6. In a spectrophone system wherein radiant energy from a radiant energy source is directed into a chamber containing a fluent sample with respect to which certain absorption data is to be obtained in the presence of background noise by detecting pressure variations within the chamber and generating a signal containing both absorption data and noise components, the radiant energy having a component corresponding to an absorption characteristic of the fluent sample which is being investigated and said chamber having a geometry allowing a resonant wave to be established in the chamber, an improved method for significantly attenuating the noise component relative to the absorption data component which comprises creating a resonant wave in the chamber, monitoring pressure variations at a location within the chamber corresponding to a peak of the resonant wave to develop a corresponding peak signal containing both true absorption data and noise components, monitoring pressure variations at a location within the chamber corresponding to a nodal point of the resonant wave and generating a corresponding nodal signal representing background noise, and modifying the peak signal by the nodal signal to remove the noise component from the peak signal and yield a true absorption data signal.

7. In a spectrophone system wherein radiant energy from a radiant energy source is directed into a chamber containing a fluent sample with respect to which certain absorption data is to be obtained in the presence of background noise by detecting pressure variations within the chamber and generating signals containing both absorption data and noise components, the radiant energy having a component corresponding to an absorption characteristic of the fluent sample which is being investigated and said chamber having a geometry allowing a resonant wave to be established in the chamber, the improvement for significantly attenuating the noise component relative to the absorption data component so as to yield a true absorption data signal comprising means creating a state of resonance in the chamber by excitation from the radiant energy source wherein a half wave or integral multiple thereof is established in the chamber, means for monitoring pressure variations at a location within the chamber corresponding to a peak point of the resonant half wave or multiple thereof and generating a peak signal containing absorption data and noise components, means for monitoring pressure variations at another location within the chamber corresponding to a point of the half wave or multiple thereof where the resultant signal when processed with the peak signal will yield a true absorption data signal, and means for processing said resultant signal with said peak signal to yield such a true absorption data signal.

8. In a spectrophone system wherein radiant energy from a radiant energy source is directed into a chamber containing a fluent sample with respect to which certain absorption data is to be obtained in the presence of background noise by detecting pressure variations within the chamber and generating signals containing both absorption data and noise components, the radiant energy having a component corresponding to an absorption characteristic of the fluent sample which is being investigated and said chamber having a geometry allowing a resonant wave to be established in the chamber, an improved method for significantly attenuating the noise component relative to the absorption data component so as to yield a true absorption data signal comprising creating a state of resonance in the chamber by excitation from the radiant energy source wherein a half wave or integral multiple thereof is established in the chamber, monitoring pressure variations at a location within the chamber corresponding to a peak point of the resonant half wave or multiple thereof and generating a peak signal containing absorption data and noise components, monitoring pressure variations at another location within the chamber corresponding to a point of the half wave or multiple thereof where the resultant signal when processed with the peak signal will yield a true absorption data signal, and processing said resultant signal with said peak signal to yield such a true absorption data signal.

* * * * *